United States Patent [19]

Leuthard

[11] 4,234,310  
[45] Nov. 18, 1980

[54] POROUS CERAMIC DENTAL FILLING INSERT

[76] Inventor: Paul E. Leuthard, Bahnhofstrasse 26, Zürich, Switzerland

[21] Appl. No.: 877,654

[22] Filed: Feb. 14, 1978

[30] Foreign Application Priority Data

Feb. 25, 1977 [CH] Switzerland .................. 2437/77

[51] Int. Cl.³ .............................................. A61K 5/01
[52] U.S. Cl. .................................................. 433/228
[58] Field of Search ............... 32/15, 10 A; 264/19, 264/20; 260/998.11; 433/228

[56] References Cited

U.S. PATENT DOCUMENTS

| | | | |
|---|---|---|---|
| 139,012 | 5/1873 | Mack | 32/15 |
| 764,871 | 7/1904 | Sparks | 32/15 |
| 1,063,376 | 6/1913 | Nies | 32/15 |
| 2,538,486 | 1/1951 | Tofflemire | 32/15 |
| 2,644,232 | 7/1953 | Roubian | 32/15 |
| 3,314,420 | 4/1967 | Smith et al. | 32/10 A |
| 4,001,939 | 1/1977 | Gross | 32/15 |
| 4,097,935 | 7/1978 | Jurcho | 32/15 |

FOREIGN PATENT DOCUMENTS 16126 10/1903 United Kingdom ............... 32/15

OTHER PUBLICATIONS

"Porous Implant Systems for Prosthesis Stabilization", Clinical Orthopaedics, No. 89, 12/1972, Homsy et al., pp. 220–224.

*Primary Examiner*—Louis G. Mancene  
*Assistant Examiner*—John J. Wilson  
*Attorney, Agent, or Firm*—Roylance, Abrams, Berdo & Farley

[57] ABSTRACT

The insert is held in place by surrounding plastic filling material and improves resistance to abrasion. Bonding to the filling material is improved by impregnation of the insert with a wetting agent or filling material. The insert may be made by extruding a porcelain paste into the desired crossection segments. Porosity of the fired material is obtained by mixing a volatile binder, such as polyethelene glycol, with the ceramic powder. Acid treatment is also disclosed for providing the desired porosity.

7 Claims, 7 Drawing Figures

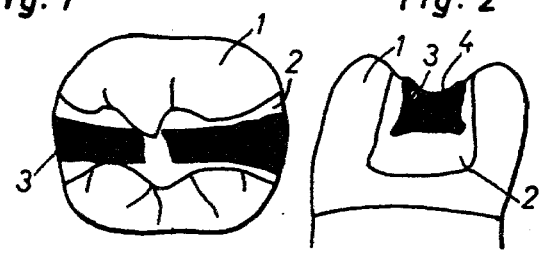
Fig. 1  Fig. 2
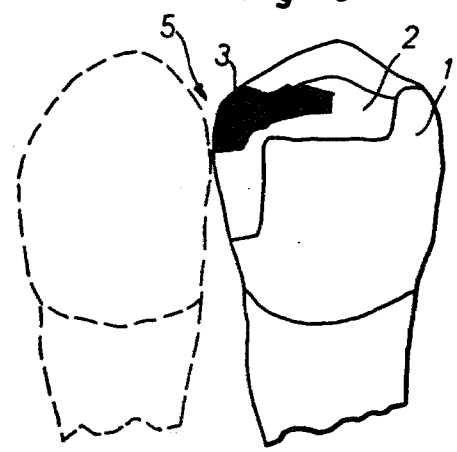
Fig. 3
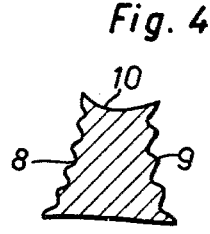 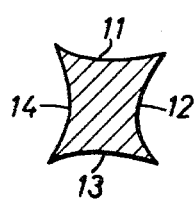 
Fig. 4  Fig. 5  Fig. 6

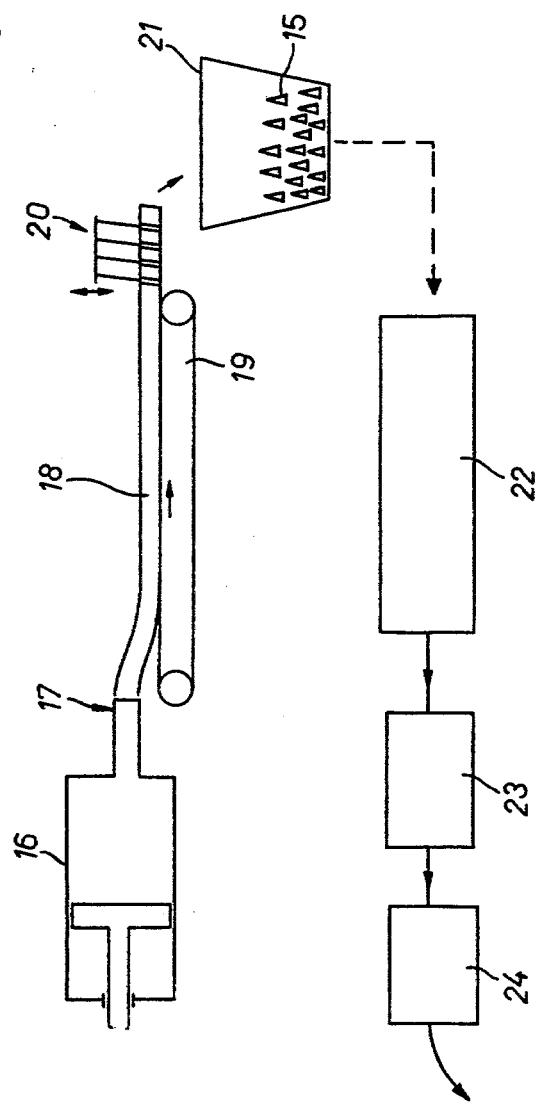

POROUS CERAMIC DENTAL FILLING INSERT

BACKGROUND OF THE INVENTION

The present invention relates to dental filling materials. The hitherto known materials for dental fillings constituted by plastics or amalgam introduced into the prepared cavity in a flowable or plastic state, and which after hardening are adapted to the natural shape of the tooth by mechanical surface treatment only, have a limited durability because they cannot permanently withstand the strong abrasive action occurring during chewing. In addition, the color of amalgam fillings is unsatisfactory.

Gold fillings are very expensive to make and involve high material costs. Gold fillings are also often undesired due to the different color compared with the tooth.

It is an object of the present invention to provide a material which makes it possible to produce in a simple manner and with low labor costs esthetically satisfactory dental fillings with an excellent resistance to wear.

BRIEF SUMMARY OF THE INVENTION

In accordance with the present invention there is provided an insert for producing dental fillings which comprises a porous ceramic material.

DETAILED DESCRIPTION

When using the insert according to the invention, the former is embedded in the cavity in a shape which is adapted to the cavity by means of a plastic filling material, so that after the plastic material has hardened it is held in the area of the tooth, which is exposed to high stresses. Final shaping then takes place in a conventional manner by mechanically contouring the filling material with the insert until adaptation to the natural shape of the tooth has been achieved. The necessary firm connection with the plastic filling material which embeds the insert is ensured due to the porosity of the insert according to the invention. To ensure good and rapid bonding between the insert and the embedding material, the insert can be impregnated with a plastic material or a wetting liquid (primer) which is joined without difficulty to the plastic embedding material. The embedding material and/or the hitherto conventional filling material comprises a plastic material with a mineral filler known as composite material, such as e.g. "Concise" and "Adaptic".

The material for producing the insert can be the same material as used for producing dental porcelain.

An improvement of the porosity of the insert or the production of open porosity on the surface for increasing the bonding strength with the filling material can be obtained by an acid treatment of an otherwise mainly closed porosity ceramic material of the insert.

The method for producing the insert comprises the following steps:

mixing ceramic powder with a volatile and pore-forming material, e.g. polyethylene glycol, to yield a pasty substance;

molding the substance to the desired shape of the insert; and firing the molded article formed in a porcelain firing oven.

The product obtained is a porous ceramic body, preferably whose shape and dimensions permits its use without subsequent mechanical treatment in the most commonly occurring cavities. Preferably, an extrusion die with a triangular discharge cross-section can be used for this purpose. The firing process can be followed by the above-mentioned acid treatment to obtain an open porosity of the insert. Impregnation with a wetting liquid (primer) or a plastic material can follow in a further process stage.

BRIEF DESCRIPTION OF THE DRAWINGS

The invention is described in greater detail hereinafter with reference to the attached drawings.

FIG. 1 is a top view of a rear molar tooth with two inserts in accordance with a preferred embodiment of the present invention.

FIG. 2 is a vertical section at right angles through the tooth of FIG. 1.

FIG. 3 is a section in the longitudinal direction of a jaw and through a front molar tooth with an insert in accordance with another embodiment of the present invention.

FIGS. 4 to 6 are various configurations of inserts in accordance with the present invention.

FIG. 7 is a schematic view of an apparatus for producing inserts in accordance with the present invention.

THE PREFERRED EMBODIMENTS

Reference is now made to the figures shown in the drawings. When using the insert, i.e. when making the filling, tooth 1 is previously drilled in the conventional manner and filled to such an extent with the conventional filling material 2 that after embedding an insert or inserts 3 in the filling material the drilled hole is filled to such an extent that sufficient material remains on the outside of the tooth to permit by mechanical treatment, such as e.g. polishing, the formation of the natural and functionally correct chewing surface shape of the tooth from the filling material and the insert material. Thus, a shaping treatment of for example the surface 4 of FIG. 2 is necessary in the same way as for conventional fillings. The arrangement of the insert or the position of its embedding in the filling material 2 must always be such that it is located in the area of maximum abrasive action when chewing or in the area of occlusal contact. Part of the mechanical treatment of the insert can take place prior to its embedding in the filling material 2, particularly at points which due to their position are difficult or impossible to work on the actual tooth, such as e.g. point 5 in the tooth of FIG. 3.

Very varied shapes can be given to the inserts, whereby as a result of the manufacture, based on an extrudate, shaping can easily be carried out on lateral surfaces 8 and 9. This shaping action can lead to a better connection of the insert to a filling or embedding material 2. Particular cross-sectional shapes of the extrudate, e.g. in accordance with FIGS. 4 and 5 so that the insert has a so-called retention shape can also contribute to a good anchoring of the insert in the embedding material 2 or the cavity. It is also advantageous to have a concave curvature of top surface 10 or the four lateral surfaces 11 to 14, leading to a good retention shape and a surface which is already substantially adapted to the chewing surface shape of the tooth.

FIG. 6 is a view of a flat insert 15 whose shape is suitable for the most frequently occurring cavity shape. More extensive adaptation to the shape of a cavity can be obtained by subsequent machining of the insert 15, when for example parts are broken away from it. This insert shape can also be produced in simple manner, based on an extrudate.

FIG. 7 diagrammatically shows an apparatus for producing the insert. A ceramic powder slurry with an emulsion is introduced into extruder 16, e.g. a screw extruder. Through a squeezing out through nozzle 17, an extrudate 18 is formed with the desired cross-sectional shape of the insert, e.g. triangular corresponding to the example of FIG. 6. By means of a conveyor 19, the extrudate 18 is fed to a cutting device 20 which cuts from it individual portions which pass into a storage container 21 from which they are supplied to a porcelain oven 22. Following the burning process, the cooled inserts can undergo acid treatment in a further apparatus 23, so that an open porous surface is formed on the inserts. Finally, the inserts can be impregnated with a wetting liquid (primer) or a plastics material in an apparatus 24.

Instead of being produced by extrusion, the moulded articles to be fired can also be formed by compression molding by providing a plurality of mold cavities in a split mold, the cavities corresponding to the shape of the inserts to be produced.

The material mixed with the ceramic powder evaporates in the oven, so that pores between 5 and $50\mu$ are formed. Due to the acid treatment, closed pores in the surface area of the insert can be opened, permitting good bonding to the embedding material. Without this porosity gaps would form between the insert and the embedding or filling material into which bacteria could penetrate.

I claim:

1. In a dental filling including a conventional plastic filling material adapted to be located in a cavity drilled in a tooth, the improvement comprising:
    a preformed, abrasive resistant, porous ceramic insert embedded in the conventional plastic filling material,
    said insert having an outer shape different from and unrelated to the shape of the cavity,
    said insert having an exposed surface adapted to be aligned with the surface of the tooth to improve resistance of the dental filling to abrasion,
    said insert being impregnated with a plastic material which forms a firm bond with the plastic filling material.
2. The improvement according to claim 1 wherein said insert has means for increasing the friction between the outer surface thereof and the contacting portions of the conventional plastic filling material to foster retention of said insert relative to said plastic filling material.
3. The improvement according to claim 1 and wherein said insert has a triangular cross-section.
4. The improvement according to claim 1 and wherein said insert has a rhombic cross-section.
5. The improvement according to claim 1 and wherein at least two of the lateral surfaces of said insert are non-planar.
6. The improvement according to claim 1 and wherein at least one side of the cross-section of said insert is a concave shape.
7. The improvement according to claim 1 and wherein the surface of said insert is open-pored with pores of between 5 and 50 micro-meters in diameter.

* * * * *